US011820731B2

(12) United States Patent
Bodas et al.

(10) Patent No.: US 11,820,731 B2
(45) Date of Patent: Nov. 21, 2023

(54) SYSTEMS AND METHODS FOR PRODUCING METHANOL WITH RECYCLING OF FUEL OIL

(71) Applicant: SABIC Global Technologies B.V., Bergen op Zoom (NL)

(72) Inventors: Vijay Dinkar Bodas, Riyadh (SA); Guillermo Leal, Riyadh (SA); Mohammed Bismillah Ansari, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 169 days.

(21) Appl. No.: 17/434,191

(22) PCT Filed: Feb. 27, 2020

(86) PCT No.: PCT/IB2020/051691
§ 371 (c)(1),
(2) Date: Aug. 26, 2021

(87) PCT Pub. No.: WO2020/178684
PCT Pub. Date: Sep. 10, 2020

(65) Prior Publication Data
US 2022/0162144 A1    May 26, 2022

Related U.S. Application Data

(60) Provisional application No. 62/815,268, filed on Mar. 7, 2019.

(51) Int. Cl.
*C07C 29/151* (2006.01)
*C07C 29/80* (2006.01)
*C07C 41/34* (2006.01)

(52) U.S. Cl.
CPC .......... *C07C 29/1518* (2013.01); *C07C 29/80* (2013.01); *C07C 41/34* (2013.01)

(58) Field of Classification Search
CPC ..... C07C 29/1518; C07C 29/80; C07C 41/34; C07C 31/04; C07C 41/06; C07C 43/046
See application file for complete search history.

(56) References Cited

U.S. PATENT DOCUMENTS

| 4,455,394 A | 6/1984 | Pinto |
| 6,258,860 B1 | 7/2001 | Weedon et al. |

(Continued)

FOREIGN PATENT DOCUMENTS

| CN | 1930104 A | 3/2007 |
| CN | 101243027 A | 8/2008 |

(Continued)

OTHER PUBLICATIONS

International Search Report and Written Opinion from PCT/IB2020/051691 dated Jun. 15, 2020, 10 pages.

(Continued)

*Primary Examiner* — Jafar F Parsa
(74) *Attorney, Agent, or Firm* — Norton Rose Fulbright US LLP

(57) ABSTRACT

A method of producing methanol is disclosed. The method involves adding alkali to crude methanol and distilling the crude methanol in one or more distillation columns. The method also includes flowing a vapor side draw from one of the distillation columns, where the vapor side draw comprises fusel oil substantially free from alkali. The fusel oil is recycled to a methanol synthesis reactor and/or a MTBE synthesis reactor.

20 Claims, 4 Drawing Sheets

(56) References Cited

U.S. PATENT DOCUMENTS

| | | | |
|---|---|---|---|
| 9,320,986 B2 | 4/2016 | Der et al. | |
| 2003/0051393 A1* | 3/2003 | Stickney | C10L 1/02 44/385 |
| 2005/0197412 A1 | 9/2005 | Van Egmond et al. | |
| 2007/0299146 A1* | 12/2007 | Lattner | C07C 1/20 518/715 |
| 2011/0214981 A1 | 9/2011 | Early | |

FOREIGN PATENT DOCUMENTS

| | | |
|---|---|---|
| CN | 102119136 A | 7/2011 |
| CN | 107746368 A | 3/2018 |
| EP | 0040481 A2 | 11/1981 |
| EP | 0040481 B1 | 7/1985 |
| EP | 0624388 A1 | 11/1994 |
| EP | 0624388 B1 | 1/1998 |
| EP | 0802893 B1 | 4/1999 |
| WO | WO2010026412 A1 | 3/2010 |

OTHER PUBLICATIONS

Li et al. Recovery and Utilization of Hetero-methanol Oil Produced from Methanol Equipment. Environmental Protection of Oil & Gas Fields, 3rd issue, Sep. 10, 2006. English Translation.

* cited by examiner

SYSTEMS AND METHODS FOR PRODUCING METHANOL WITH RECYCLING OF FUEL OIL

CROSS REFERENCE TO RELATED APPLICATIONS

This application is a national phase application under 35 U.S.C. § 371 of International Application No. PCT/IB2020/051691 filed Feb. 27, 2020, which claims priority to U.S. Provisional Patent Application No. 62/815,268 filed Mar. 7, 2019. The entire contents of each of the above-referenced disclosures is specifically incorporated by reference herein without disclaimer.

FIELD OF INVENTION

The present invention generally relates to the production of methanol. More specifically, the present invention relates to the production of methanol, in a process where fuel oil is recycled to produce synthesis gas and/or methyl tertiary butyl ether (MTBE).

BACKGROUND OF THE INVENTION

Methanol ($CH_3OH$) is an essential raw material used for producing a variety of chemicals such as formaldehyde, acetic acid, and MTBE. On the industrial scale, methanol is commonly produced by reacting carbon monoxide (CO) and hydrogen ($H_2$) from synthesis gas in the presence of a catalyst as shown below.

$$CO + 2H_2 \rightarrow CH_3OH$$

The production process may also include reacting carbon dioxide with hydrogen to form methanol as shown below.

$$CO_2 + 3H_2 \rightarrow CH_3OH + H_2O$$

The methanol production process results in the formation of a by-product known as fuel oil (fuel alcohol). The phrase "fuel oil" as used herein denotes organic compounds having a higher boiling point than methanol ($CH_3OH$) and formed as by-products during catalytic methanol synthesis. Crude methanol from the methanol product process comprises methanol and fuel oil. The crude methanol is refined in distillation units to remove fuel oil and other materials. Typically, prior to distillation, a solution of an alkali is added to neutralize organic acids in the crude methanol, the unreacted portion of which, if not eventually removed, can corrode metals in the distillation unit. Distillation typically produces a refined methanol stream, a fuel oil stream, and a water stream. The alkali remains dissolved in the fuel oil stream and the water stream. It is expensive to remove the alkali that remains in the fuel oil stream. Thus, currently, fuel oil from methanol production units is burnt—an inefficient use of such hydrocarbon resources.

BRIEF SUMMARY OF THE INVENTION

A method has been discovered for producing methanol that addresses at least some of the above problems with conventional methods of producing methanol. The discovered method involves recycling the fuel oil by-product from the methanol production process to produce synthesis gas and/or MTBE, without the need to remove alkali from the recycled fuel oil.

Embodiments of the invention include a method of producing methanol that comprises reacting carbon dioxide ($CO_2$) and/or carbon monoxide (CO) with hydrogen ($H_2$) in a reactor to produce crude methanol. The method further comprises adding an alkali to the crude methanol to produce a crude methanol/alkali mixture and separating, in a separation unit comprising one or more distillation columns, the crude methanol/alkali mixture into a plurality of streams. The plurality of streams comprise: (1) an overhead stream comprising primarily methanol, (2) a bottoms stream comprising primarily water and alkali, collectively, and (3) a vapor side draw stream comprising primarily fuel oil, wherein the vapor side draw stream comprises less than 100 ppb alkali. The method further includes recycling the vapor side draw stream to one or more of: (a) a reformer adapted to produce synthesis gas and (b) a methyl tertiary butyl ether (MTBE) synthesis reactor.

Embodiments of the invention include a method of producing methanol and/or MTBE that comprises reacting carbon dioxide ($CO_2$) and/or carbon monoxide (CO) with hydrogen ($H_2$) in a reactor to produce crude methanol. The method further comprises adding an alkali to the crude methanol to produce a crude methanol/alkali mixture and separating, in a first distillation column, the crude methanol/alkali mixture into a (A) an overhead intermediate stream comprising dimethyl ether and (B) a bottoms intermediate stream comprising primarily methanol, water, alkali, and ethanol. The method also includes separating, in a second distillation column, the bottoms intermediate stream into a plurality of streams comprising: (1) an overhead stream comprising primarily methanol, (2) a bottoms stream comprising primarily water and alkali, collectively, and (3) a vapor side draw stream comprising primarily fuel oil. The vapor side draw stream comprises less than 100 ppb alkali. Further, the separating in the second distillation column comprises extracting the vapor side draw stream from the second distillation column by operation of one or more of: (1) a jet ejector, (2) a steam eductor, and (3) a heat exchanger adapted to cool and condense the vapor side draw stream. The method further includes recycling the vapor side draw stream to one or more of: (a) a reformer adapted to produce synthesis gas and (b) a methyl tertiary butyl ether (MTBE) synthesis reactor.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for producing methanol, in which fusel oil by-product from the methanol production process is recycled to produce synthesis gas and/or MTBE. The recycled fusel oil has a limited amount of alkali so that there is no need to remove alkali from the recycled fusel oil.

Figure 1:
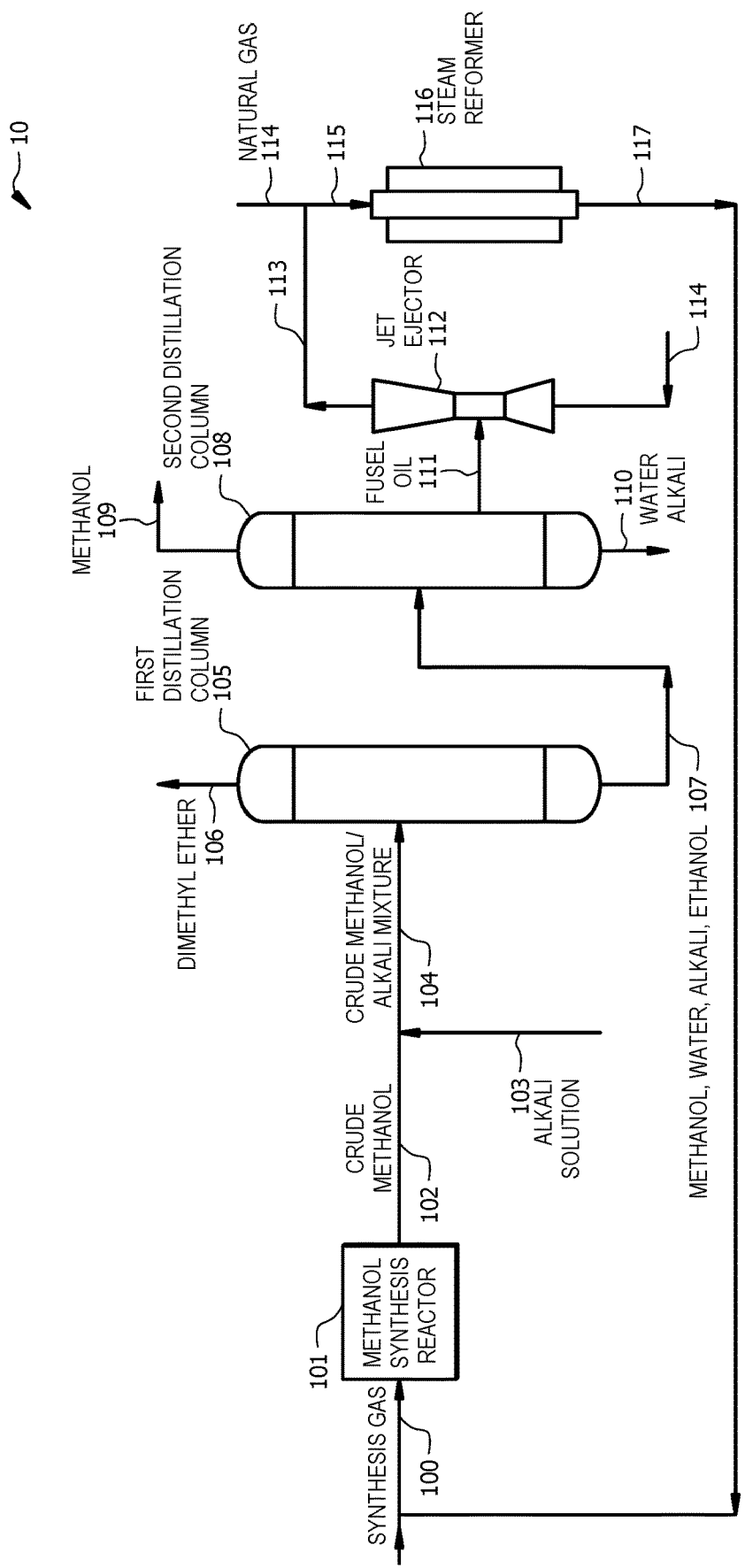
FIG. 1 shows a system for producing methanol, according to embodiments of the invention.
Figure 2:
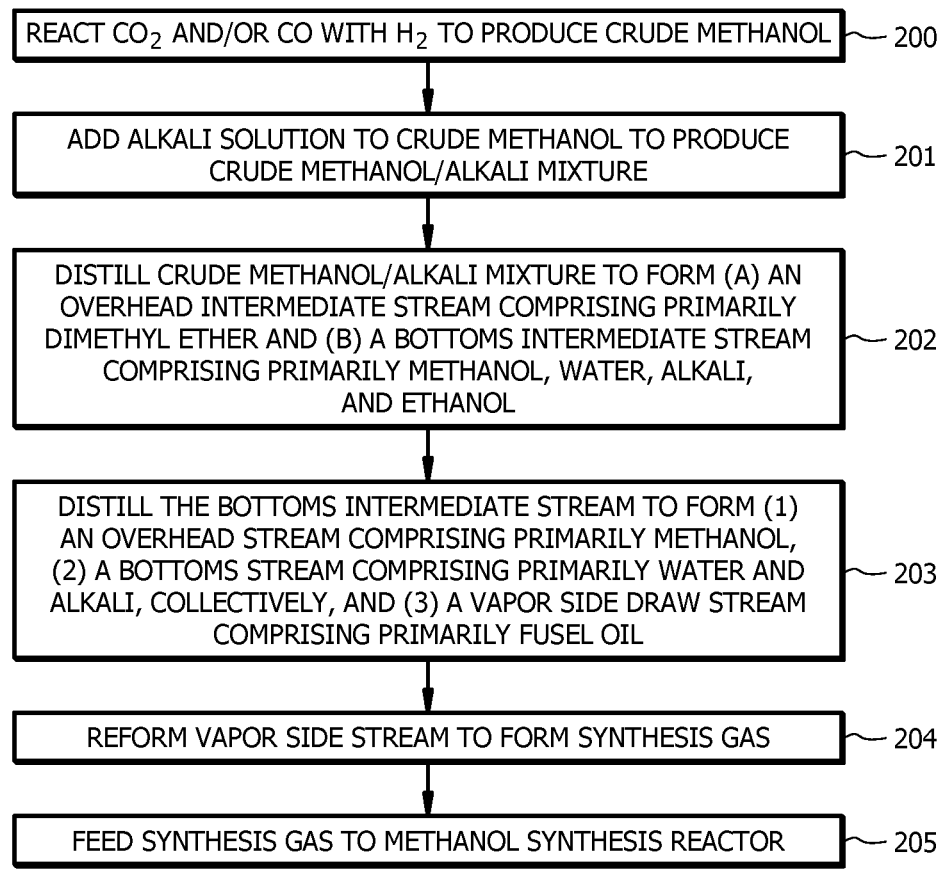
FIG. 2 shows a method for producing methanol, according to embodiments of the invention.

FIG. 1 shows system 10 for producing methanol, according to embodiments of the invention. FIG. 2 shows method 20 for producing methanol, according to embodiments of the invention. Method 20 may be implemented using system 10.

Method 20, according to embodiments of the invention, includes, at block 200, reacting carbon dioxide ($CO_2$) and/or carbon monoxide (CO) with hydrogen ($H_2$) to produce crude methanol, in methanol synthesis reactor 101. Typically, the carbon monoxide, carbon dioxide and hydrogen are from synthesis gas (synthesis gas 100, in FIG. 1). At block 201, in embodiments of the invention, method 20 further comprises adding alkali solution 103 to crude methanol 102 to produce crude methanol/alkali mixture 104, in an effort to reduce the corrosive effects of organic acids that may be in crude methanol 102.

At block 202, according to embodiments of the invention, method 20 includes distilling crude methanol mixture containing a small amount of dosed alkali to remove light ends such as dimethyl ether from methanol. Thus, as illustrated, method 20 can involve separating, in first distillation column 105, crude methanol/alkali mixture 104 into (A) overhead intermediate stream 106 comprising primarily dimethyl ether and (B) bottoms intermediate stream 107 comprising primarily methanol, water, alkali, and ethanol, collectively, in embodiments of the invention. In embodiments of the invention, operating conditions of first distillation column 105 include a bottom column temperature in a range of 100° C. to 150° C. and all ranges and values there between including ranges of 100 to 105° C., 105 to 110° C., 110 to 115° C., 115 to 120° C., 120 to 125° C., 125 to 130° C., 130 to 135° C., 135 to 140° C., 140 to 145° C., and 145 to 150° C.; a top column temperature in a range of 60° C. to 75° C. and all ranges and values there between including ranges of 60 to 63° C., 63 to 66° C., 66 to 69° C., 69 to 72° C., and 72 to 75° C.; and a pressure in a range of 1.2 bar absolute to 8 bar absolute and all ranges and values there between including ranges of 1.2 to 1.6 bar absolute, 1.6 to 2.0 bar absolute, 2.0 to 2.4 bar absolute, 2.4 to 2.8 bar absolute, 2.8 to 3.2 bar absolute, 3.2 to 3.6 bar absolute, 3.6 to 4.0 bar absolute, 4.0 to 4.4 bar absolute, 4.4 to 4.8 bar absolute, 4.8 to 5.2 bar absolute, 5.2 to 5.6 bar absolute, 5.6 to 6.0 bar absolute, 6.0 to 6.4 bar absolute, 6.4 to 6.8 bar absolute, 6.8 to 7.2 bar absolute, 7.2 to 7.6 bar absolute, and 7.6 to 8.0 bar absolute. In embodiments of the invention, 99 wt. % of the dimethyl ether in crude methanol 102 is recovered in overhead intermediate stream 106. In embodiments of the invention, overhead intermediate stream 106 comprises 40 to 60 wt. % dimethyl ether and 60 to 40 wt. % methanol. In embodiments of the invention, bottoms intermediate stream 107 comprises 75 to 85 wt. % methanol, 15 to 25 wt. % water, 10 to 120 ppm alkali, and 150 to 1000 ppm ethanol.

Method 20, in embodiments of the invention, includes, at block 203, separating, in second distillation column 108, bottoms intermediate stream 107 into a plurality of streams comprising: (1) overhead stream 109 comprising primarily methanol, (2) bottoms stream 110 comprising primarily water and alkali, collectively, and (3) vapor side draw stream 111 comprising primarily fusel oil, wherein vapor side draw stream 111 comprises less than 100 ppb wt. % alkali. Second distillation column 108 is a methanol product column where methanol is obtained overhead. In embodiments of the invention, operating conditions of second distillation column 108 include a bottom column temperature in a range of 100 to 150° C. and all ranges and values there between including ranges of 100 to 105° C., 105 to 110° C., 110 to 115° C., 115 to 120° C., 120 to 125° C., 125 to 130° C., 130 to 135° C., 135 to 140° C., 140 to 145° C., and 145 to 150° C., and a top column temperature in a range of 60 to 75° C. and all ranges and values there between including ranges of 60 to 63° C., 63 to 66° C., 66 to 69° C., 69 to 72° C., and 72 to 75° C.; and a pressure in a range of 1.2 bar absolute to 8 bar absolute and all ranges and values there between including ranges of 1.2 to 1.6 bar absolute, 1.6 to 2.0 bar absolute, 2.0 to 2.4 bar absolute, 2.4 to 2.8 bar absolute, 2.8 to 3.2 bar absolute, 3.2 to 3.6 bar absolute, 3.6 to 4.0 bar absolute, 4.0 to 4.4 bar absolute, 4.4 to 4.8 bar absolute, 4.8 to 5.2 bar absolute, 5.2 to 5.6 bar absolute, 5.6 to 6.0 bar absolute, 6.0 to 6.4 bar absolute, 6.4 to 6.8 bar absolute, 6.8 to 7.2 bar absolute, 7.2 to 7.6 bar absolute, and 7.6 to 8.0 bar absolute. In embodiments of the invention, overhead stream 109 comprises a minimum of 99.85 wt. % methanol and a maximum of 0.1 wt. % water. In embodiments of the invention, overhead stream 109 comprises 99.8 to 99.9 wt. % methanol, maximum 0.1 wt. % water, maximum 0.003 wt. % acetone and aldehydes, and maximum 0.01 wt. % ethanol. The bottoms of distillation column 108 is waste water, according to embodiments of the invention. In embodiments of the invention, bottoms stream 110 comprises a total organic carbon content of 500 ppm. In embodiments of the invention, 99.9% of water, alkali, and sodium compounds collectively in the crude methanol are recovered in bottoms stream 110. In embodiments of the invention, bottoms stream 110 comprises 99 to 100 wt. % water, 50 to 600 ppm alkali, and maximum total organic carbon content of 500 ppm. The separating block 203, in embodiments of the invention, comprises extracting vapor side draw stream 111 from second distillation column 108 by jet ejector 112. In embodiments of the invention, vapor side draw stream 111 is taken from the sixth to the eighth tray above the bottom tray.

According to embodiments of the invention, the tray from which vapor side draw stream 111 is drawn is a tray where heavy alcohol byproducts (e.g., ethanol and butanol, formed in methanol synthesis reactor 101) concentrates (e.g., the tray with the highest concentration of heavy alcohol byproducts (fusel oil)). Second distillation column 108, according to embodiments of the invention, is a low pressure column operated with its overhead pressure being 1.2 to 1.6 bar absolute. In embodiments of the invention, jet ejector 112 (e.g., a steam jet ejector) draws vapor side draw stream 111 from near the bottom of second distillation column 108 such that vapor side draw stream 111 comprises 100 ppb alkali, a minimum of 97 wt. % fusel oil, and a maximum of 1 wt. % water. Having vapor side draw stream 111, in embodiments of the invention, ensures that the alkali present in crude methanol/alkali mixture 104 remains in waste water of bottoms stream 110 flowing from the bottom of second distillation column 108. Further, because of the composition of vapor side draw stream 111, for example where vapor side draw stream 111 has a minimal amount of water (maximum of 10 wt. % to maximum 1 wt. %, depending on operating days in life of methanol synthesis converter catalyst related changes in fusel oil make), embodiments of the invention do not require a separation process to remove unwanted materials such as water prior to recycling vapor side draw stream 111 to the reformer or the MTBE synthesis reactor, as may be needed for liquid-phase side draws, for which water can have significantly higher quantities of undesirable sodium hydroxide. In this way, the cost of equipment for carrying out such separation can be avoided.

Motive steam 114 is used to drive jet ejector 112 and becomes a part of the steam dosed to steam reformer inlet as a part of normal steam reforming requirement. Motive steam 114, sent to the jet ejector 112, can be flowed through a steam to carbon ratio control system that controls steam to carbon ratio based on metering and/or using average fixed values of the amount of steam, natural gas, and fusel oil. Adding motive steam 114 to the steam to carbon ratio control system can reduce the amount of steam otherwise flowing to steam reformer 116. In this way, the carbon ratio control system is able to maintain steam to carbon ratio the same with or without jet ejector 112. Thus, jet ejector 112 and vapor side draw stream 111 can be brought online when required and shut off without disrupting the steam reforming operation. Vapor side draw/steam mixture 113, comprising higher alcohols, is routed to steam reformer 116, where vapor side draw/steam mixture 113 is reformed to produce synthesis gas 117 (i.e. part of synthesis gas 100), at block 204. According to embodiments of the invention, at block 205, synthesis gas 100 is then fed to methanol synthesis reactor 101, where synthesis gas 100 is used to make methanol as described with respect to the reactions discussed in the background above.

Figure 3:
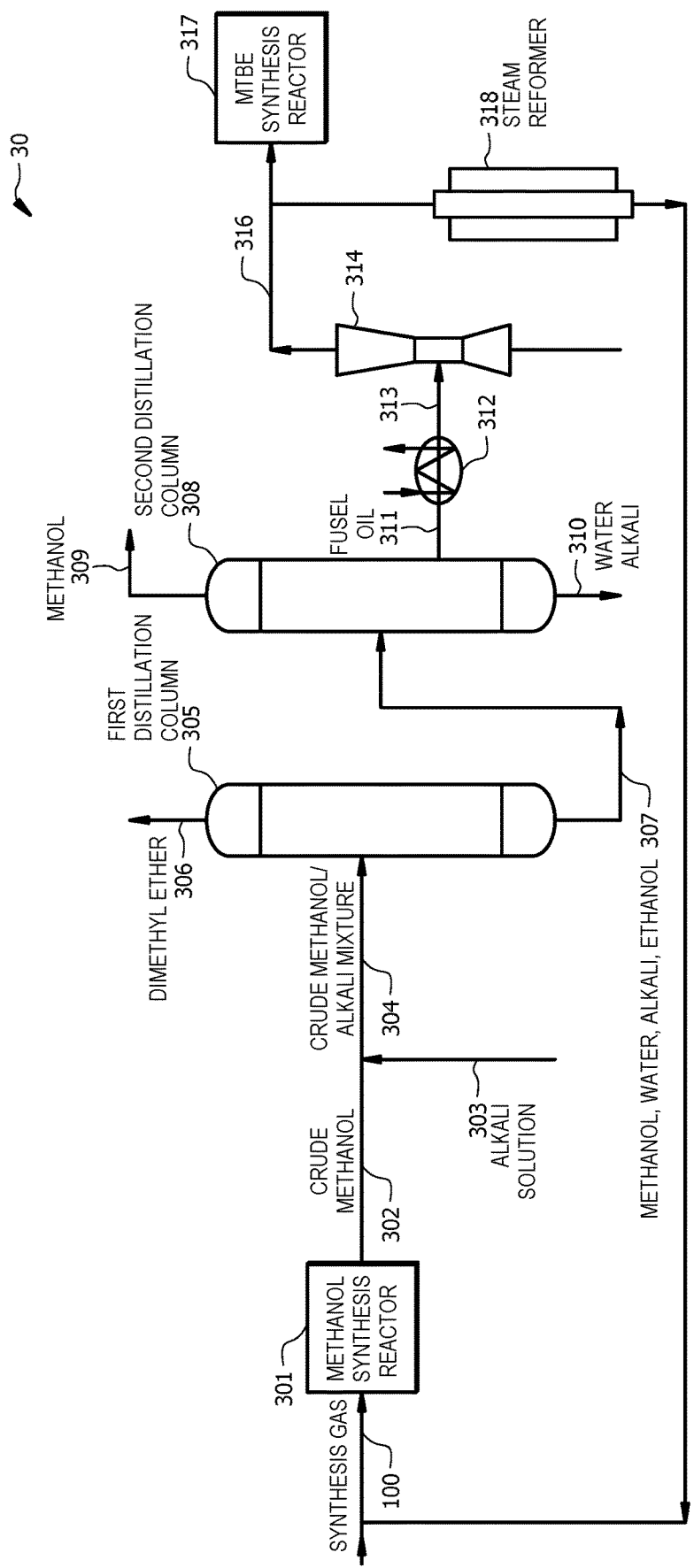
FIG. 3 shows a system for producing methanol and/or MTBE, according to embodiments of the invention.
Figure 4:
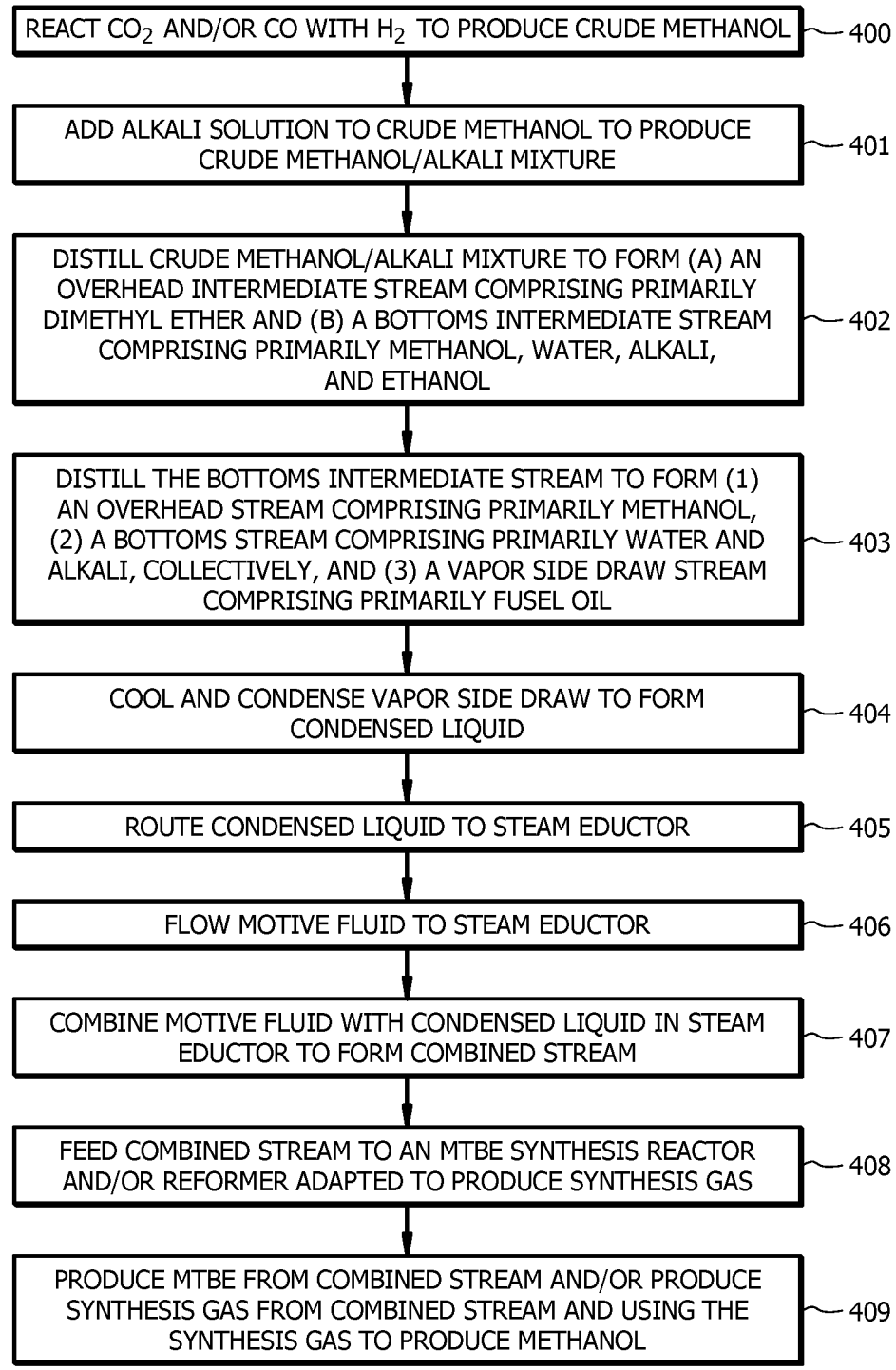
FIG. 4 shows a method for producing methanol and/or MTBE, according to embodiments of the invention.

FIG. 3 shows system 30 for producing methanol and/or MTBE, according to embodiments of the invention. FIG. 4 shows method 40 for producing methanol and/or MTBE, according to embodiments of the invention. Method 40 may be implemented using system 30.

System 30 shows a scheme where there is co-production of methanol and MTBE. Method 40, according to embodiments of the invention, includes, at block 400, reacting carbon dioxide ($CO_2$) and/or carbon monoxide (CO) with hydrogen ($H_2$) to produce crude methanol, in methanol synthesis reactor 301. Typically, the carbon monoxide, carbon dioxide and hydrogen are from synthesis gas (synthesis gas 300, in FIG. 3). At block 401, in embodiments of the invention, method 40 further comprises adding alkali solution 303 to crude methanol 302 to produce crude methanol/alkali mixture 304, in an effort to reduce the corrosive effects of organic acids that may be in crude methanol 302.

At block 402, according to embodiments of the invention, method 40 includes distilling crude methanol mixture containing a small amount of dosed alkali to remove light ends such as dimethyl ether from methanol. Thus, as illustrated, method 40 involves separating, in first distillation column 305, crude methanol/alkali mixture 304 into (A) overhead intermediate stream 306 comprising primarily dimethyl ether and (B) bottoms intermediate stream 307 comprising primarily methanol, water, alkali, and ethanol, collectively, in embodiments of the invention. In embodiments of the invention, operating conditions of first distillation column 305 include a bottom column temperature in a range of 100° C. to 150° C. and all ranges and values there between including ranges of 100 to 105° C., 105 to 110° C., 110 to 115° C., 115 to 120° C., 120 to 125° C., 125 to 130° C., 130 to 135° C., 135 to 140° C., 140 to 145° C., and 145 to 150° C.; a top column temperature in a range of 60° C. to 75° C. and all ranges and values there between including ranges of 60 to 63° C., 63 to 66° C., 66 to 69° C., 69 to 72° C., and 72 to 75° C.; and a pressure in a range of 1.2 bar absolute to 8 bar absolute and all ranges and values there between including ranges of 1.2 to 1.6 bar absolute, 1.6 to 2.0 bar absolute, 2.0 to 2.4 bar absolute, 2.4 to 2.8 bar absolute, 2.8 to 3.2 bar absolute, 3.2 to 3.6 bar absolute, 3.6 to 4.0 bar absolute, 4.0 to 4.4 bar absolute, 4.4 to 4.8 bar absolute, 4.8 to 5.2 bar absolute, 5.2 to 5.6 bar absolute, 5.6 to 6.0 bar absolute, 6.0 to 6.4 bar absolute, 6.4 to 6.8 bar absolute, 6.8 to 7.2 bar absolute, 7.2 to 7.6 bar absolute, and 7.6 to 8.0 bar absolute. In embodiments of the invention, 99 wt. % of the dimethyl ether in crude methanol 302 is recovered in overhead intermediate stream 306. In embodiments of the invention, overhead intermediate stream 306 comprises 40 to 60% dimethyl ether and 60 to 40% methanol. In embodiments of the invention, bottoms intermediate stream 307 comprises 75 to 85 wt. % methanol, 15 to 25 wt. % water, 10 to 120 ppm alkali, and 150 to 1000 ppm ethanol.

Method 40, in embodiments of the invention, includes, at block 403, separating, in second distillation column 308, bottoms intermediate stream 307 into a plurality of streams comprising: (1) overhead stream 309 comprising primarily methanol, (2) bottoms stream 310 comprising primarily water and alkali, collectively, and (3) vapor side draw stream 311 comprising primarily fusel oil, wherein vapor side draw stream 311 comprises less than 100 ppb wt. % alkali. Second distillation column 308 is a methanol product column where methanol is obtained overhead as overhead stream 309. In embodiments of the invention, operating conditions of second distillation column 308 include a bottom column temperature in a range of 100 to 150° C. and all ranges and values there between including ranges of 100 to 105° C., 105 to 110° C., 110 to 115° C., 115 to 120° C., 120 to 125° C., 125 to 130° C., 130 to 135° C., 135 to 140° C., 140 to 145° C., and 145 to 150° C., and a top column temperature in a range of 60 to 75° C. and all ranges and values there between including ranges of 60 to 63° C., 63 to 66° C., 66 to 69° C., 69 to 72° C., and 72 to 75° C., and a pressure in a range of 1.2 bar absolute to 8 bar absolute and all ranges and values there between including ranges of 1.2 to 1.6 bar absolute, 1.6 to 2.0 bar absolute, 2.0 to 2.4 bar absolute, 2.4 to 2.8 bar absolute, 2.8 to 3.2 bar absolute, 3.2 to 3.6 bar absolute, 3.6 to 4.0 bar absolute, 4.0 to 4.4 bar absolute, 4.4 to 4.8 bar absolute, 4.8 to 5.2 bar absolute, 5.2 to 5.6 bar absolute, 5.6 to 6.0 bar absolute, 6.0 to 6.4 bar absolute, 6.4 to 6.8 bar absolute, 6.8 to 7.2 bar absolute, 7.2 to 7.6 bar absolute, and 7.6 to 8.0 bar absolute. In embodiments of the invention, overhead stream 309 comprises a minimum of 99.85 wt. % methanol and a maximum of 0.1 wt. % water. In embodiments of the invention, overhead stream 309 comprises 99.8 to 99.9 wt. % methanol, maximum 0.1 wt. % water, maximum 0.003 wt. % acetone and aldehydes, and maximum 0.1 wt. % ethanol. The bottoms of distillation column 308 is waste water, according to embodiments of the invention. In embodiments of the invention, bottoms stream 310 comprises a total organic carbon content of 500 ppm. In embodiments of the invention, 99.9% of water, alkali, and sodium compounds collectively in the crude methanol are recovered in bottoms stream 310. In embodiments of the invention, bottoms stream 310 comprises 99 to 100 wt. % water, 50 to 600 ppm alkali, and maximum total organic content of 500 ppm.

According to embodiments of the invention, vapor side draw stream 311 is drawn from a tray where heavy alcohol byproducts (e.g., ethanol and butanol, formed in methanol synthesis reactor 301) concentrate (e.g., a tray with the highest concentration of heavy alcohol by-products (fusel oil)). In embodiments of the invention, vapor side draw stream 311 comprises 100 ppb alkali, a minimum of 97 wt. % fusel oil, and a maximum of 1 wt. % water. Second distillation column 308, according to embodiments of the invention, is a low pressure column operated with its overhead pressure being 1.2 to 1.6 bar absolute. Having vapor side draw stream 311, in embodiments of the invention, ensures that the alkali present in crude methanol/alkali mixture 304 remains in waste water of bottoms stream 310 flowing from the bottom of second distillation column 308. Further, because of the composition of vapor side draw stream 311, for example where vapor side draw stream 311 has a minimal amount of water (maximum of 10 wt. % to maximum 1 wt. %, depending on operating days in life of methanol synthesis converter catalyst related changes in fusel oil make), embodiments of the invention do not require a separation process to remove unwanted materials such as water prior to recycling vapor side draw stream 311 to the reformer or the MTBE synthesis reactor, as may be needed for liquid-phase side draws, for which water can contain significantly higher content of undesirable sodium hydroxide, which is expensive to separate. In this way, the cost of equipment for carrying out such separation can be avoided.

In embodiments of the invention, method 40 includes, at block 404, cooling and condensing vapor side draw stream 311 by heat exchanger 312 to form condensed liquid 313. At block 405, in embodiments of the invention, condensed liquid 313 is routed to steam eductor 314. The effect of the condensation of vapor side draw stream 311 and the operation of steam eductor 314 at blocks 404 and 405 draws vapor side draw stream 311 from near the bottom of second distillation column 308. According to embodiments of the invention, method 40, includes, at block 406, flowing motive fluid 315 to steam eductor 314. Flowing motive fluid 315, in embodiments of the invention, comprises flowing a liquid methanol stream that is normally fed to MTBE synthesis reactor 317. In embodiments of the invention, at block 407, motive fluid 315 combines with condensed liquid 313 in steam eductor 314 to form combined stream 316. At block 408, according to embodiments of the invention, method 40 includes routing combined stream 316 to MTBE synthesis reactor 317 and/or reformer 318, adapted to produce synthesis gas. In embodiments of the invention, block 409 involves producing MTBE from combined stream 316 and/or producing synthesis gas from combined stream 316 and using the synthesis gas to produce methanol. The MTBE production in embodiments of the invention include reacting methanol with isobutylene. The methanol production, in embodiments of the invention, is as described with respect to the reactions discussed in the background above.

Method 20 can be implemented as an alternative to method 40 or in combination with method 40. For example, two side draw streams may be implemented, a first implemented as described in method 20 and a second implemented as described in method 40.

According to embodiments of the invention, in method 40, motive fluid 315 (methanol feed) is already under sufficient pressure needed to flow motive fluid 315 to MTBE synthesis reactor 317, thus no additional moving equipment is required and steam eductor 314 and the condensing effect together are sufficient to pull vapor side draw stream 311 from second distillation column 308. The small amount of ethanol/butanol in condensed liquid 313 forms respective ether byproducts in MTBE synthesis reactor 317. These heavy alcohols are small enough in quantity in condensed liquid 313 and combined stream 316 such that it does not disrupt purity of MTBE nor does it alter its octane number. The heavy alcohols can have a beneficial effect on Reid vapor pressure of the MTBE produced. In embodiments of the invention, the Reid vapor pressure of the MTBE produced is in a range of 7.0 to 8.0 psi and all ranges and values there between including ranges of 7.0 to 7.2 psi, 7.2 to 7.4 psi, 7.4 to 7.6 psi, 7.6 to 7.8 psi, 7.8 to 8.0 psi.

Although embodiments of the present invention have been described with reference to blocks of FIG. 2 and FIG. 4, it should be appreciated that operation of the present invention is not limited to the particular blocks and/or the particular order of the blocks illustrated in FIG. 2 and FIG. 4. Accordingly, embodiments of the invention may provide functionality as described herein using various blocks in a sequence different than that of FIG. 2 and FIG. 4.

In the context of the present invention, at least the following 16 embodiments are described. Embodiment 1 is a method of producing methanol. The method includes reacting carbon dioxide ($CO_2$) and/or carbon monoxide (CO) with hydrogen ($H_2$) in a reactor to produce crude methanol and adding an alkali to the crude methanol to produce a crude methanol/alkali mixture. The method further includes separating, in a separation unit having one or more distillation columns, the crude methanol/alkali mixture into a plurality of streams including: (1) an overhead stream containing primarily methanol, (2) a bottoms stream containing primarily water and alkali, collectively, and (3) a vapor side draw stream containing primarily fusel oil, wherein the vapor side draw stream contains less than 100 ppb alkali. The method also includes recycling the vapor side draw stream to one or more of: (a) a reformer adapted to produce synthesis gas and (b) a methyl tertiary butyl ether (MTBE) synthesis reactor. Embodiment 2 is the method of embodiment 1, wherein the separating includes distilling, in a first distillation column, the crude methanol/alkali mixture into a (A) an overhead intermediate stream containing dimethyl ether and (B) a bottoms intermediate stream containing primarily methanol, water, alkali, and ethanol. The method further includes distilling, in a second distillation column, the bottoms intermediate stream into a plurality of streams including: (1) the overhead stream, (2) the bottoms stream, and (3) the vapor side draw stream. Embodiment 3 is the method of embodiment 2, wherein 99 wt. % of dimethyl ether from the crude methanol is recovered in the overhead intermediate stream. Embodiment 4 is the method of either of embodiments 2 or 3, wherein the separating includes extracting the vapor side draw stream from the second distillation column by operation of one or more of: (1) a jet ejector, (2) a steam eductor, and (3) a heat exchanger adapted to cool and condense the vapor side draw stream. Embodiment 5 is the method of embodiment 4, wherein the vapor side draw stream is extracted from a tray that is one of the sixth to the eighth tray from the bottom tray of the second distillation column. Embodiment 6 is the method of embodiment 4, wherein the vapor side draw stream is extracted from a tray of the second distillation column that collects material that has the highest concentration of fusel oil. Embodiment 7 is the method of any of embodiments 1 to 6, wherein the carbon dioxide, the carbon monoxide, and the hydrogen are from synthesis gas. Embodiment 8 is the method of any of embodiments 1 to 7, wherein operating conditions of the first distillation column include a bottom column temperature in a range of 100° C. to 150° C. and a top column temperature in a range of 60° C. to 75° C. and a pressure in a range of 1.2 bar absolute to 8 bar absolute. Embodiment 9 is the method of any of embodiments 1 to 8, wherein operating conditions of the second distillation column include a bottom column temperature in a range of 100° C. to 150° C. and a top column temperature in a range of 60° C. to 75° C. and a pressure in a range of 1.2 bar absolute to 8 bar absolute. Embodiment 10 is the method of any of embodiments 1 to 9, wherein the overhead stream contains a minimum of 99.85 wt. % methanol and a maximum of 0.1 wt. % water. Embodiment 11 is the method of any of embodiments 1 to 10, wherein the bottoms stream includes a total organic carbon content of 500 ppm. Embodiment 12 is the method of any of embodiments 1 to 11, wherein of 99.9% of water, alkali, and sodium compounds collectively in the crude methanol are recovered in the bottoms stream. Embodiment 13 is the method of any of embodiments 1 to 12, wherein the vapor side draw stream contains 100 ppb alkali, a minimum of 97 wt. % fusel oil, and a maximum of 1 wt. % water. Embodiment 14 is the method of any of embodiments 1 to 12, wherein the vapor side draw stream comprises 100 ppb alkali, a minimum of 89 wt. % fusel oil, and a maximum of 10 wt. % water. Embodiment 15 is the method of any of claims 1 to 14, wherein Reid vapor pressure of the MTBE from the synthesis reactor is in a range of 7.0 to 8.0 psi. Embodiment 16 is the method of any of embodiments 1 to 14, wherein the vapor side draw stream is not subjected to a separation process prior to recycling to the reformer or the MTBE synthesis reactor.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing methanol, the method comprising:
    reacting carbon dioxide ($CO_2$) and/or carbon monoxide (CO) with hydrogen ($H_2$) in a reactor to produce crude methanol;
    adding an alkali to the crude methanol to produce a crude methanol/alkali mixture;
    separating, in a separation unit comprising a first distillation column and a second distillation column, the crude methanol/alkali mixture into a plurality of streams comprising: (1) an overhead stream comprising primarily methanol, (2) a bottoms stream comprising primarily water and alkali, collectively, and (3) a vapor side draw stream comprising primarily fusel oil, wherein the vapor side draw stream comprises less than 100 ppb alkali, a minimum of 89 wt. % fusel oil, and a maximum of 10 wt. % water;
    recycling the vapor side draw stream to one or more of: (a) a reformer adapted to produce synthesis gas and (b) a methyl tertiary butyl ether (MTBE) synthesis reactor;
    wherein the separating comprises:
        distilling, in the first distillation column, the crude methanol/alkali mixture into (A) an overhead intermediate stream comprising dimethyl ether and (B) a bottoms intermediate stream comprising primarily methanol, water, alkali, and ethanol;
        distilling, in the second distillation column, the bottoms intermediate stream into a plurality of streams comprising: (1) the overhead stream, (2) the bottoms stream, and (3) the vapor side draw stream; and
        extracting the vapor side draw stream from the second distillation column by operation of one or more of: (1) a jet ejector, (2) a steam eductor, and (3) a heat exchanger adapted to cool and condense the vapor side draw stream.

2. The method of claim 1, wherein the vapor side draw stream is recycled to the methyl tertiary butyl ether synthesis reactor.

3. The method of claim 1, wherein the vapor side draw stream is recycled to the methyl tertiary butyl ether synthesis reactor and 99 wt. % of dimethyl ether from the crude methanol is recovered in the overhead intermediate stream.

4. The method of claim 2, wherein the separating comprises extracting the vapor side draw stream from the second distillation column by operation of the jet ejector.

5. The method of claim 4, wherein the vapor side draw stream is extracted from a tray that is one of the sixth to the eighth tray from the bottom tray of the second distillation column.

6. The method of claim 4, wherein the vapor side draw stream is extracted from a tray of the second distillation column that collects material that has the highest concentration of fusel oil.

7. The method of claim 1, wherein the carbon dioxide, the carbon monoxide, and the hydrogen are from synthesis gas.

8. The method of claim 1, wherein operating conditions of the first distillation column include a bottom column temperature in a range of 100° C. to 150° C. and a top column temperature in a range of 60° C. to 75° C. and a pressure in a range of 1.2 bar absolute to 8 bar absolute.

9. The method of claim 1, wherein operating conditions of the second distillation column include a bottom column temperature in a range of 100° C. to 150° C. and a top column temperature in a range of 60° C. to 75° C. and a pressure in a range of 1.2 bar absolute to 8 bar absolute.

10. The method of claim 1, wherein the overhead stream comprises a minimum of 99.85 wt. % methanol and a maximum of 0.1 wt. % water.

11. The method of claim 1, wherein the bottoms stream comprises a total organic carbon content of 500 ppm.

12. The method of claim 1, wherein of 99.9% of water, alkali, and sodium compounds collectively in the crude methanol are recovered in the bottoms stream.

13. The method of claim 1, wherein the vapor side draw stream comprises a minimum of 97 wt. % fusel oil, and a maximum of 1 wt. % water.

14. The method of claim 1, wherein the vapor side draw stream comprises a maximum of 1 wt. % water.

15. The method of claim 1, wherein Reid vapor pressure of the MTBE from the synthesis reactor is in a range of 7.0 to 8.0 psi.

16. The method of claim 1, wherein the vapor side draw stream is not subjected to a separation process prior to recycling to the reformer or the MTBE synthesis reactor.

17. The method of claim 2, wherein the separating comprises extracting the vapor side draw stream from the second distillation column by operation of a jet ejector.

18. The method of claim 2, wherein the separating comprises extracting the vapor side draw stream from the second distillation column by operation of a steam eductor.

19. The method of claim 2, wherein the separating comprises extracting the vapor side draw stream from the second distillation column by operation of a heat exchanger adapted to cool and condense the vapor side draw stream.

20. The method of claim 1, wherein Reid vapor pressure of the MTBE from the synthesis reactor is 7.0 psi.

* * * * *